(12) United States Patent
Penhorwood et al.

(10) Patent No.: US 9,823,062 B2
(45) Date of Patent: Nov. 21, 2017

(54) INSPECTION SYSTEM FOR THREADED PARTS

(71) Applicant: Mectron Engineering Company, Saline, MI (US)

(72) Inventors: Ian Kent Penhorwood, Ypsilanti, MI (US); Mark Lee Hanna, Saline, MI (US)

(73) Assignee: MECTRON ENGINEERING COMPANY, INC., Saline, MI (US)

( * ) Notice: Subject to any disclaimer, the term of this patent is extended or adjusted under 35 U.S.C. 154(b) by 189 days.

(21) Appl. No.: 14/773,151

(22) PCT Filed: Oct. 30, 2013

(86) PCT No.: PCT/US2013/067383
§ 371 (c)(1),
(2) Date: Sep. 4, 2015

(87) PCT Pub. No.: WO2014/137408
PCT Pub. Date: Sep. 12, 2014

(65) Prior Publication Data
US 2016/0018214 A1    Jan. 21, 2016

Related U.S. Application Data

(60) Provisional application No. 61/773,887, filed on Mar. 7, 2013.

(51) Int. Cl.
G01B 11/00 (2006.01)
G01N 21/00 (2006.01)
G01N 21/95 (2006.01)
G01N 21/952 (2006.01)
G01B 11/24 (2006.01)
G01B 11/245 (2006.01)

(52) U.S. Cl.
CPC ........ *G01B 11/2425* (2013.01); *G01B 11/245* (2013.01); *G01B 11/2433* (2013.01); *G01N 21/95* (2013.01); *G01N 21/952* (2013.01)

(58) Field of Classification Search
CPC   G01B 11/2425; G01B 11/2433; G01N 21/95; G01N 21/952
See application file for complete search history.

(56) References Cited

U.S. PATENT DOCUMENTS 3,650,397 A * 3/1972 Bornemeier ............. B07C 5/10
                                                          209/585
4,315,688 A * 2/1982 Pryor ..................... G01B 11/22
                                                          356/237.1

(Continued)

FOREIGN PATENT DOCUMENTS

EP    0 481 515 A2    10/1991

OTHER PUBLICATIONS

PCT International Search Report—dated Mar. 28, 2014.

*Primary Examiner* — Tri Ton
*Assistant Examiner* — Jarreas C Underwood
(74) *Attorney, Agent, or Firm* — Brinks Gilson & Lione (57) ABSTRACT

The present invention relates to an inspection device and particularly to a device using an array of light sources and photo-detection devices to evaluate threaded workpieces for conformance to spatial form criteria. The invention provides for improved identification of flaws in threaded components to identify the conformance of parts.

12 Claims, 9 Drawing Sheets

(56) References Cited

U.S. PATENT DOCUMENTS

| | | | | |
|---|---|---|---|---|
| 4,395,119 A | * | 7/1983 | Nakata | G01B 11/08 |
| | | | | 250/559.24 |
| 4,576,482 A | * | 3/1986 | Pryor | G01B 11/2433 |
| | | | | 209/538 |
| 4,831,251 A | * | 5/1989 | Hanna | G01B 11/2425 |
| | | | | 209/929 |
| 4,880,991 A | * | 11/1989 | Boehnlein | G01B 11/08 |
| | | | | 250/559.15 |
| 5,139,150 A | * | 8/1992 | Fuller, Jr. | B07C 5/10 |
| | | | | 198/345.1 |
| 5,383,021 A | | 1/1995 | Hanna | |
| 5,568,263 A | | 10/1996 | Hanna | |
| 5,646,724 A | * | 7/1997 | Hershline | G01N 21/952 |
| | | | | 250/223 R |
| 6,252,661 B1 | | 6/2001 | Hanna | |
| 6,285,034 B1 | | 9/2001 | Hanna et al. | |
| 6,313,948 B1 | | 11/2001 | Hanna | |
| 7,738,121 B2 | * | 6/2010 | Spalding | G01B 11/028 |
| | | | | 250/559.24 |
| 7,777,900 B2 | * | 8/2010 | Nygaard | G01B 11/2425 |
| | | | | 356/635 |
| 2005/0174567 A1 | * | 8/2005 | Hanna | G01N 21/952 |
| | | | | 356/237.1 |
| 2010/0039655 A1 | * | 2/2010 | Crowther | G01B 11/2433 |
| | | | | 356/601 |

* cited by examiner

INSPECTION SYSTEM FOR THREADED PARTS

CROSS REFERENCE TO RELATED APPLICATIONS

This application claims priority to U.S. Provisional Patent Application No. 61/773,887, filed Mar. 7, 2013, and PCT/US2013/067383, filed Oct. 30, 2013.

FIELD OF THE INVENTION

The present invention relates to a device for inspecting components and particularly to a device using an array of light sources and photo-detection devices for evaluating threaded workpieces for conformance to spatial form criteria.

BACKGROUND OF THE INVENTION

Presently, there is an ever increasing demand to obtain high quality products which has resulted in a significant increase in the use of non-contact inspection systems. In order for a complex machine to operate as designed, it is necessary that all of its sub-components comply with quality criteria. In some manufacturing settings, many customers require 100% inspection of component parts. For example, flanged or headed fasteners used in the automobile industry and elsewhere often must be individually inspected to determine if they meet spatial form criteria.

Numerous types of inspection systems are presently utilized. One type of system uses contact probes which touch a component at various points to determine if its dimension or profiles meet certain criteria. However, contact devices have inherent limitations in that they are subject to wear and generally require that the component and the contact probe be accurately positioned during the evaluation process. Moreover, such devices are generally slow to operate and are limited in terms of the number of criteria and complexity of profiles which they can evaluate. A variety of non-contact systems are also known using a variety of techniques. For example, ultrasonic inspection systems examine reflected sound waves as a means of characterizing a component. Various systems based on photo detection utilizing single channel photo detectors are also known. In addition, laser gauging systems are used in which specific dimensional measurements can be obtained.

Although non-contact inspection systems are presently in use, there are numerous improvements to non-contact systems that continue to provide advancements in accuracy and capability. Conformance of threaded workpieces is an area of particular importance requiring improved inspection systems to ensure workpiece conformance. There is a need in the art for a noncontact gauging system for improved inspection of threaded workpieces to improve identification of non-conforming parts.

SUMMARY OF THE INVENTION

In accordance with the present invention, an improved non-contact inspection system is provided which provides for improved identification of flaws in threaded components to identify parts in conformance or out of conformance with spatial form criteria. When producing fasteners, the process often begins with wire stock which is fed into a cold heading or screw type forming machine. The part is die-formed or cut in a machine into a shape that may include several diameters and possibly a threaded or knurled length. The formed part may require secondary operations such as thread rolling, heat treating, planning, stamping etc. It is not uncommon for one or more of the processes to fail to produce the desired geometry of part. Specifically, threaded parts may have a number of defects that can have adversely affect the function of the threaded part. Left unidentified, these defects may cause significant issues in various manufacturing and assembly applications. The occurrence of such defects is often not adequately monitored through random part selection or other quality assurance processes which do not provide a 100% inspection.

In the present invention parts move by gravity or other means along a track through a test section. The part shape is determined through the use of an array of lasers or other light sources and photo detection devices such as CCD in line pixel arrays or single channel photo detectors, but is not limited to such approaches. The array of lasers is mounted in radial fashion about a track in which the parts slide down. As a part slides down the track it will occlude the light generated from the array of lasers. The photo detection devices will measure the occluded light and generate output signals to a signal processor. From these output signals the threaded workpieces may be determined through the use of a novel method for improved measurement and detection of thread defects and geometric variation disclosed herein.

Further objects, features and advantages of this invention will become readily apparent to persons skilled in the art after a review of the following description, with reference to the drawings and claims that are appended to and form a part of this specification.

DETAILED DESCRIPTION OF THE PRESENTLY PREFERRED EMBODIMENTS

Figure 1:
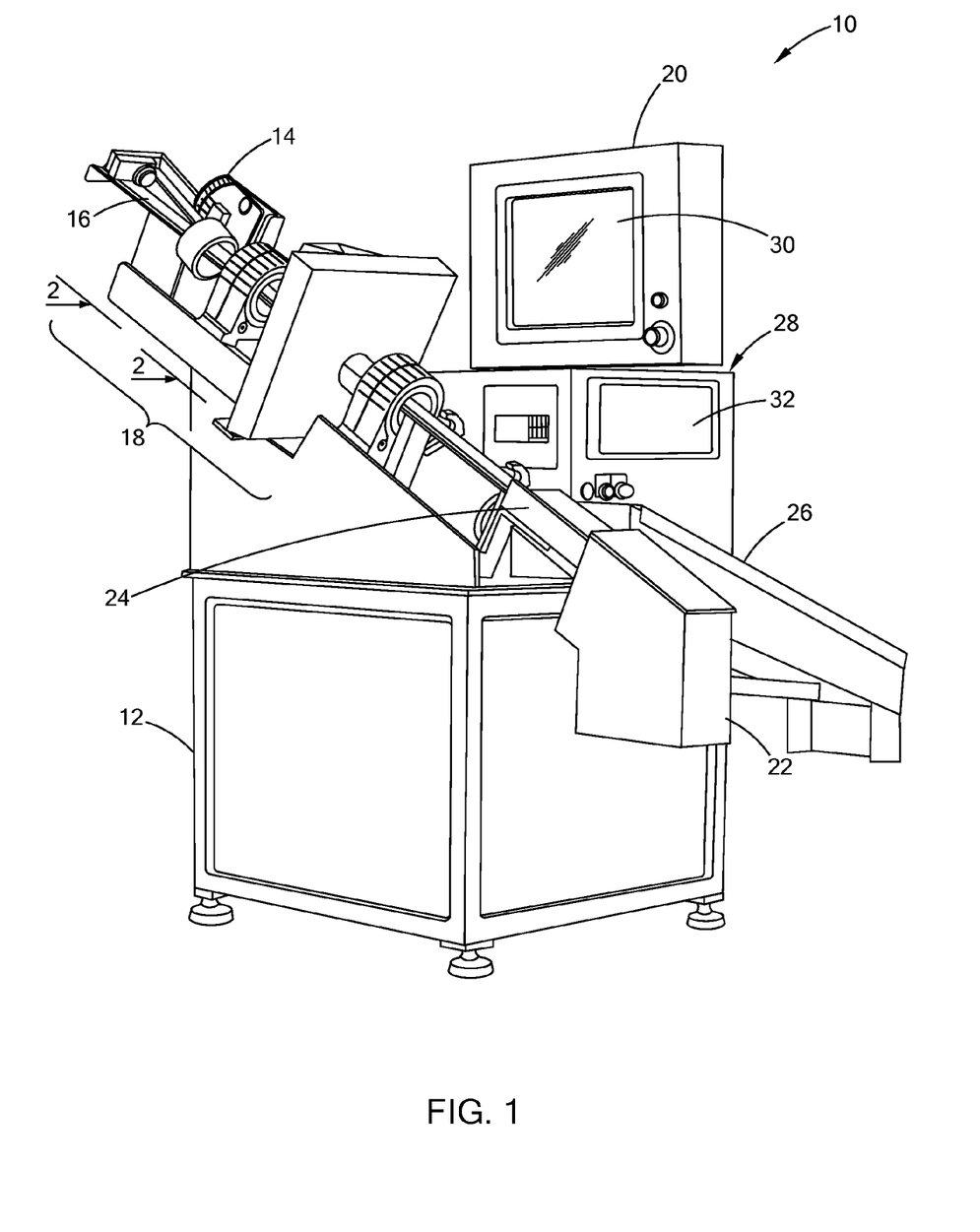
FIG. 1 is a pictorial view of the non-contact inspection system in accordance with the present invention.

FIG. 1 shows a non-contact inspection system in accordance with the present invention and is generally shown as 10. The inspection system 10 generally comprises a frame 12, parts sorter 14, slide track 16 having test section 18, and an enclosure 20 for housing electronic components of the instrument.

While the inspection system 10 can be used for numerous types of workpieces, such as square or hex head flange fastener, external Torx™, flats on a shaft, and external splines, the present invention generally relates to scanning threaded fasteners. The inspection system generally operates by inspecting fasteners passing down a track. A large number of the fasteners (also referred to as parts or work-pieces) are deposited in a part sorter bin 14. The part sorter bin 14 causes the randomly oriented fasteners to be directed in a desired orientation i.e. headed or threaded end first, and causes them to periodically slide down track 16 under the force of gravity. As fasteners pass through test section 18, they are evaluated as will be described in more detail in the following portions of this specification. The fasteners are inspected for conformance with predetermined spatial form criteria. If a particular part meets the criteria, it passes into parts chute 22 leading to a parts bin provided for qualified or conforming parts. If, however, the part is deemed to be out of conformance, gate 24 is actuated and the part is diverted into parts chute 26 for disqualified or non-conforming parts.

Figure 2:
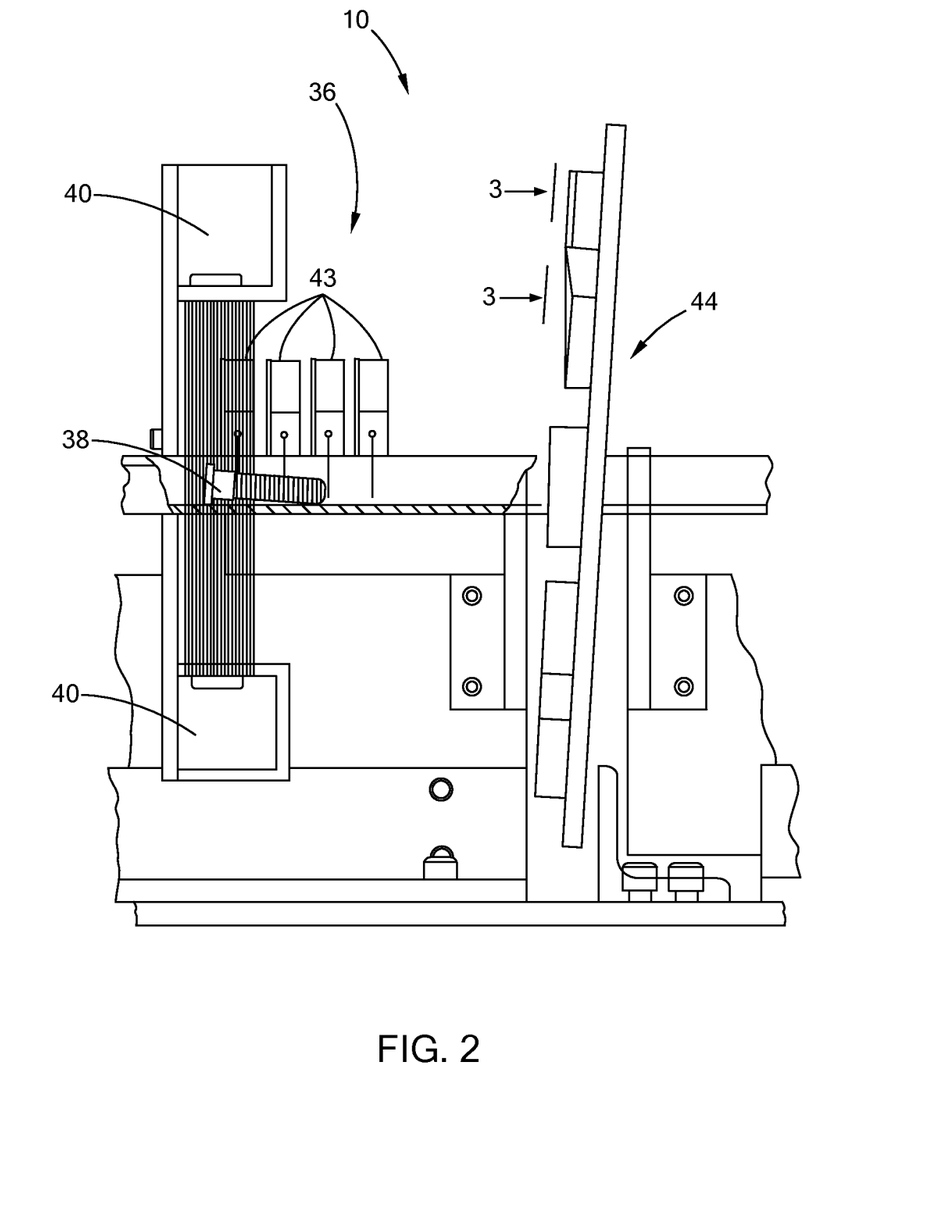
FIG. 2 is a diagrammatic drawing illustrating the photo detection system of the present invention.

Within enclosure 20 is housed a computer 28 provided for evaluating the outputs of the system, controlling the system, and electronically communicating with system memory to store information related to part criteria and inspection history. At least one display 30, 32 is incorporated in the system providing a user interface for system control and to review inspection data. The enclosure further comprises access panels which allow for access inside the housing. The general operation and elements of the inspection system 10 will be described with reference to FIGS. 2 and 3. Referring first to FIG. 2, a diagrammatic drawing illustrating the inspection system 10 in conformance with the teachings of the present invention is shown. A length test section 36 evaluates a workpiece 38 for length conformance. The workpiece 38 passes through a magnetic imager 40 that provides a metallurgic profile of the workpiece 38 to test for critical metallurgical defects such as cracks, material mixes, conductive plating's, and hardness by a visual deviation. The rate of the workpiece 38 (i.e. its velocity as it passes along the test track) is measured and evaluated by a plurality of cascading sensors 43 that are configured to detect the presence of the workpiece 38 and calculate the velocity. The velocity of the workpiece 38 allows the inspection system 10 to extrapolate information related to the length of the workpiece 38 from profile test data. After passing through the length test section 36, the profile test section 44 measures and evaluates the radial profiles of the workpiece 38 (i.e. its form perpendicular to its longitudinal axis).

Figure 3:
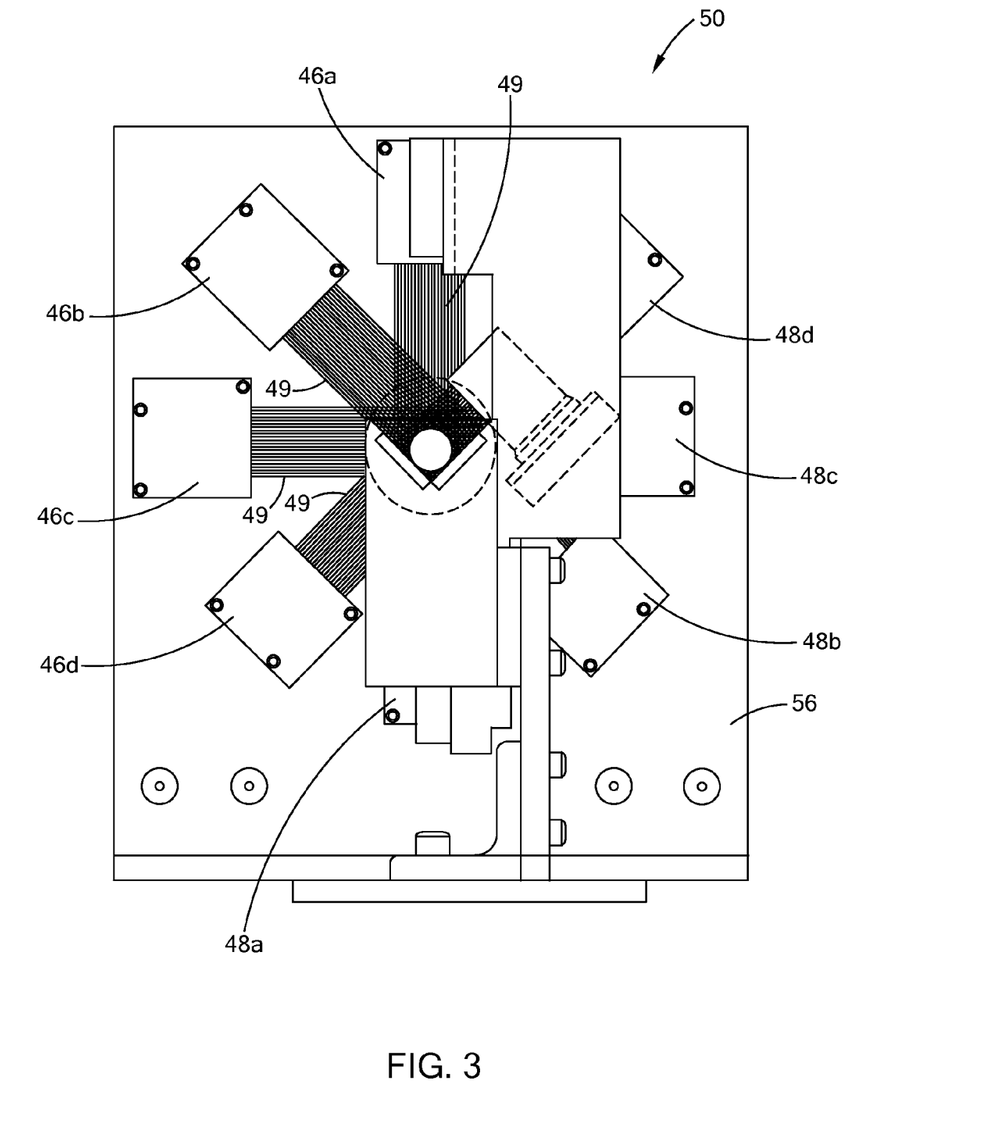
FIG. 3 is a view taken along line 3-3 of FIG. 2 particularly showing the profile detection system in accordance with the present invention.

Referring now to FIG. 3, a pictorial view taken along line 3-3 of FIG. 2, illustrating the profile test section 44 is shown in conformance with the disclosure. The radial profile of each workpiece 38 is evaluated by one or more paired profile detection devices consisting of a laser light source 46 (46*a*-46*d*) and a photo detection device 48 (48*a*-48*d*). In this implementation the paired devices are denoted with same suffix, for example, laser light source 46*a* is paired with photo detection device 48*a*. Each laser light source 46 is aligned with a corresponding photo detection device 48 to detect an occluded sheet of light 49 from the aligned laser light source 46.

In the present implementation the laser light sources 46 and photo detection devices 48 are spaced radially about the test track 16 at 45° intervals, but in another implementation the spacing may be 30° or another interval suited for an application. More generally the laser light sources 46 and photo detection devices 48 define a profile detection system 50 having one or more pairs of light sources 46 and detectors 48. In implementations utilizing a plurality of paired profile detection devices, the devices may be being evenly spaced radially about the track or oriented in other configurations for others applications. Although lasers have been detailed with some particularity, it will be understood that any coherent or non-coherent light source can be used with the present invention. All such light sources are therefore considered to be equivalents of the disclosed lasers, so long as the above general operating parameters are met. The output signals from detection devices 48 may be in the form of a signal indicating light intensity incident on each of a plurality of individual photo sensitive regions defining pixels. As such, edges of the shadow of laser light incident on the detection devices 48 can be located as particular photo sensitive regions where a significant change in incident light intensity occurs. In another approach, the signals from each photosensitive region can be summed and an associated computing device could simply provide an indication of the number of photosensitive regions which are illuminated, without necessarily identifying particular pixels where high and low intensities are present. Detection devices 48 may also be embodied in a device having separated linear arrays which may join in a cold linear manner at a position where the center of the shadow of light from light sources 46 would be occluded by the presence of a workpiece 38.

The detection devices 48 may comprise any apparatus capable of sensing light, but the preferred embodiment utilizes a CCD in line pixel array. The CCD in line pixel array is an electronic imaging device which contains a linear row of discrete photo sensing elements or pixels which convert incident light into an electrical signal. The CCD in line pixel array generates an output signal composed of a plurality of digital and analog signals. The output signals are transferred to a signal processing device where the signals are preferably converted to digital information. This digital information may be used for a gray scale output or may be processed by software for edge detection.

CCD in line arrays can operate with data ranges at very high speeds and produce many scans per second. The data is also available immediately whereas a particular line from an area sensor is only available after the lines preceding it have been read out. Furthermore, in a CCD in line array the lines are sequential and are available one right after another. This makes CCD in line arrays ideally suited for applications where motion is present. The present disclosure teaches of linear arrays being aligned perpendicular or nearly perpendicular to a longitudinal axis of a workpiece and being significantly aligned with a plurality of threads of the workpiece. This disclosure provides for improved measurement of threaded workpieces and detection of flaws thereof with improved accuracy by aligning each of the paired profile detection devices generally perpendicular to the longitudinal axis of each workpiece and each sheet of light 49 significantly parallel to the thread pitch or lead angle of the workpiece.

Figure 4:
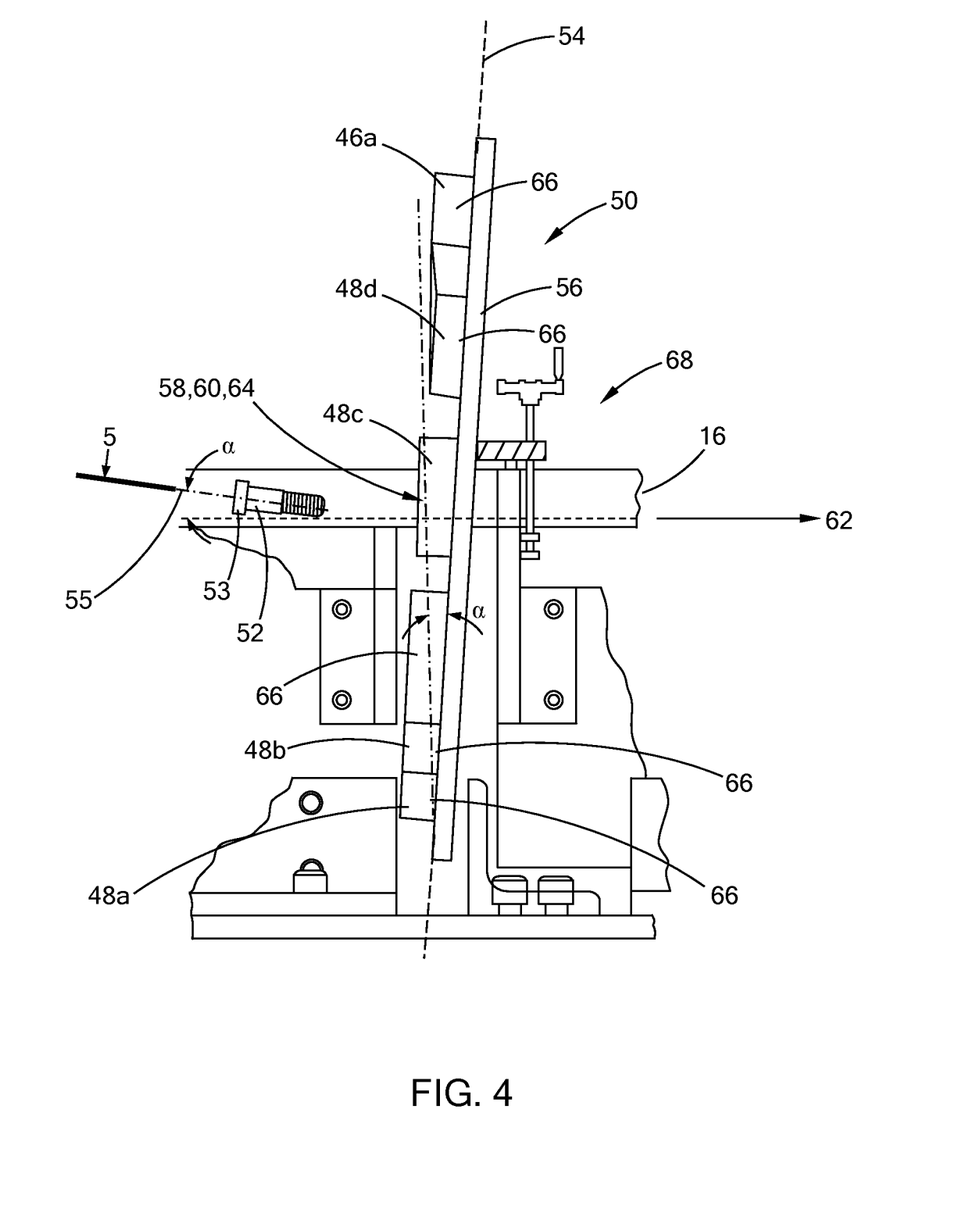
FIG. 4 is a detailed diagrammatic drawing illustrating the photo detection system of the present invention.
Figure 5:
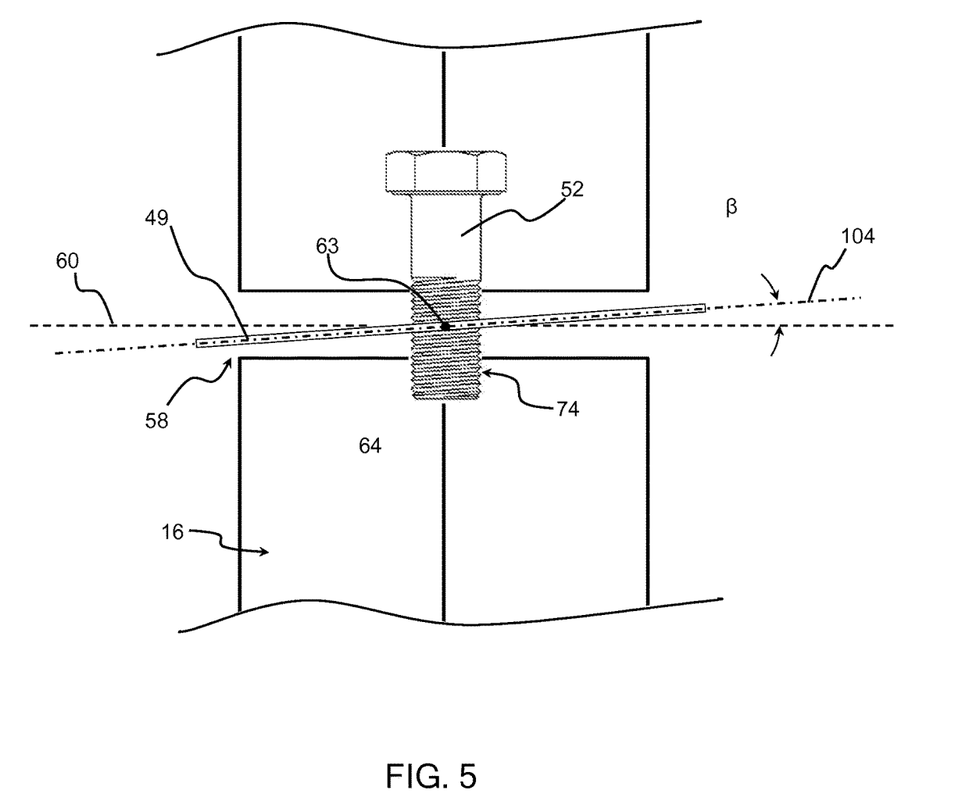
FIG. 5 is a detailed pictorial view of the sheet of light projected onto a sample planar surface in accordance with the present invention.

Referring now to FIGS. 4 and 5, a detailed diagrammatic drawing illustrating the profile detection system 50 of the present invention is shown. A workpiece 52 is shown on the track 16, creating an angle relative to the track defining a work piece angle α. For the workpiece 52 shown in FIG. 4, the presence of a head portion 53 causes a longitudinal axis 55 of the workpiece 52 to be angled at the workpiece angle α with respect to the longitudinal axis 62 of the track 16 as it passes through the profile detection system 50. In general, the profile detection system 50 of the present implementation may be significantly aligned with an inspection plane 54 being configured to adjustably align perpendicular to the longitudinal axis 55 of the workpiece 52. The workpiece angle α is demonstrated twice in FIG. 4 to demonstrate that the workpiece angle α is the same as the angular rotation a of the inspection plane in relation to the longitudinal axis 62 of the track 16.

Each light source 46 may further be configured to project a sheet of light 49 substantially aligned with the inspection plane 54. Each sheet of light 49 is defined by a beam plane 104 and may have a width w greater than its thickness t (see FIGS. 5 and 6). Each sheet of light 49 may further be projected at the test section 60 at an angle offset from the inspection plane about an axis perpendicular to the workpiece defining a beam pitch angle β, as shown in FIG. 5. In this implementation, each of the plurality of light sources and detectors, may be mounted to a mounting plate 56 configured such that the mounting plate may be adjusted angularly to align perpendicular to the workpiece angle α. Further, each sheet of light 49 emitted from each light source 46 may define a beam axis 63 intersecting with each workpiece parallel to the inspection plane 54, and the inspection plane being perpendicular to the workpiece angle α. Irrespective of the particular choice of device for light source 46, sheet of light 49 can be characterized as parallel rays of light (i.e. collimated), such that occlusion of the sheet of light by a workpiece 38 casts a sharp edge shadow onto photodetectors 48 (some diffraction effect is however expected). Light of this character can be produced by a large number of individual laser diode elements arranged in a linear array. Alternatively, through use of appropriate optics, light from a single laser source can be spread to form sheet of light 49 with the desired collimation.

The light sources 46 may be directed centrally at a cut out portion 58 of the track 16, perpendicular to the workpiece 52 defining a test section 60. Each of the light sources 46 may further be configured to project each sheet of light 49 having a width w greater than its thickness t. To further improve the accuracy of the inspection system, the beam plane 104 defining the width w each sheet of light 49 may further be aligned significantly parallel to the thread pitch of each workpiece at an angle defining a beam pitch angle β about the beam axis 63. Each beam axis 63 may be defined as extending parallel to the inspection plane 54 along the projected direction of each sheet of light 49 from each light source 46 and intersecting perpendicular or nearly perpendicular to the longitudinal axis of the workpiece.

The beam pitch angle β may similarly be described as a lead angle defining the inclination of the beam along the longitudinal axis 55 of the workpiece 52. The width w of each sheet of light 49 may further define a beam plane 104 oriented at the beam pitch angle β about the beam axis 63 intersecting the workpiece 52. Though illustrated as extending along the center of the width w of the sheet of light 49, the beam axis 63 need not align with the center of the sheet of light 49. The beam axis is provided as a reference line or axis 63 projected from the light source intersecting each workpiece, about which the beam pitch angle β is defined. The orientation of the sheets of light 49 described herein may allow for the width w of each sheet of light 49 to extend parallel to the lead or pitch angle of many fasteners. This disclosure provides for substantial improvement in measurement accuracy the system is configured such that each of the paired profile detection devices is oriented as described herein with respect to the workpiece angle α and a beam pitch angle β. Further, the beam pitch angle β may provide for significant improvement in measurement results even in cases where the alignment of the beam pitch angle β is within three degrees of the fastener thread pitch or lead angle of the threads. The inclination of sheet of light 49 provided by beam pitch angle β allows the full profile of threads of a threaded workpiece 38 to be evaluated in more detail. Without inclination provided by beam pitch angle β the threads of such a workpiece would partially obscure the thread profile.

The sheets of light 49 projected from the light sources 46 may pass through the test section 60 and be received by the detectors 48. Each paired light source 46a and detector 48a may be aligned to emit and receive a sheet of light 49 being projected centrally along the corresponding beam plane 104. Though each pair of inspection devices comprising the light source 46a, 46b, 46c, 46d and the detector 48a, 48b, 48c, 48d respectively are aligned to emit and receive a corresponding sheets of light 49, each paired light source and detector must be mirrored across the test section 60. In other words, due to the fact that a paired the light source 46a and detector 48a face each other, the orientation of the light source 46a and the detector 48a must be mirrored to align the paired devices along the beam plane 104.

For ease of understanding, the track 16 may further be defined as an x-axis 62 in an orthogonal coordinate system arranged about an origin 64 defined as the cut out portion 58 of the profile test section 60. As the workpiece 52 translates along the x-axis 62 through the profile test section 60 comprising the origin 64 and the cutout portion 58 of the disclosed invention, each of the light sources 46 may project a sheet of light 49 onto the workpiece such that the beam axis 63 of the sheet of light 49 is substantially perpendicular to the longitudinal axis 55 of the workpiece and parallel to the inspection plane 54. The beam axis 63 of the sheet of light 49 is shown in FIG. 5 as dot for clarity.

The orientation of the of each beam axis 63 of each sheet of light 49 perpendicular to the longitudinal axis 55 of each workpiece 52 allows the length of each workpiece 52 to pass through the sheets of light as the workpiece 52 translates through the profile test section 60. The light sources 46 and detectors in this implementation are each shown enclosed in a plurality of housings 66 attached to the mounting plate 56. Each housing 66 orients each of the light sources 46 and detectors with the beam plane 104 at the beam pitch angle β rotated about the beam axis 63 relative to the mounting plate. The beam axis 63 of each sheet of light 49 is substantially perpendicular to the longitudinal axis 55 of the workpiece and parallel to the inspection plane 54. In this implementation the housings 66 have an angled geometry in relation to the inspection plane 54, but projecting each sheet of light 49 at an angle may be accomplished by other enclosures or housings, some of which are introduced in FIGS. 7A to 7C.

The term substantially as used herein with respect to alignment and angular orientation is used to incorporate variation in assembly and manufacture of the disclosed system and a range of angles approaching those described herein in which the disclosed system will still provide for substantial improvements. The system disclosed may provide for improvements even if the mounting plate may be within 10 degrees of the inspection plane and the beam pitch angle is be within 3 degrees of the thread pitch of the workpiece.

Figure 6:
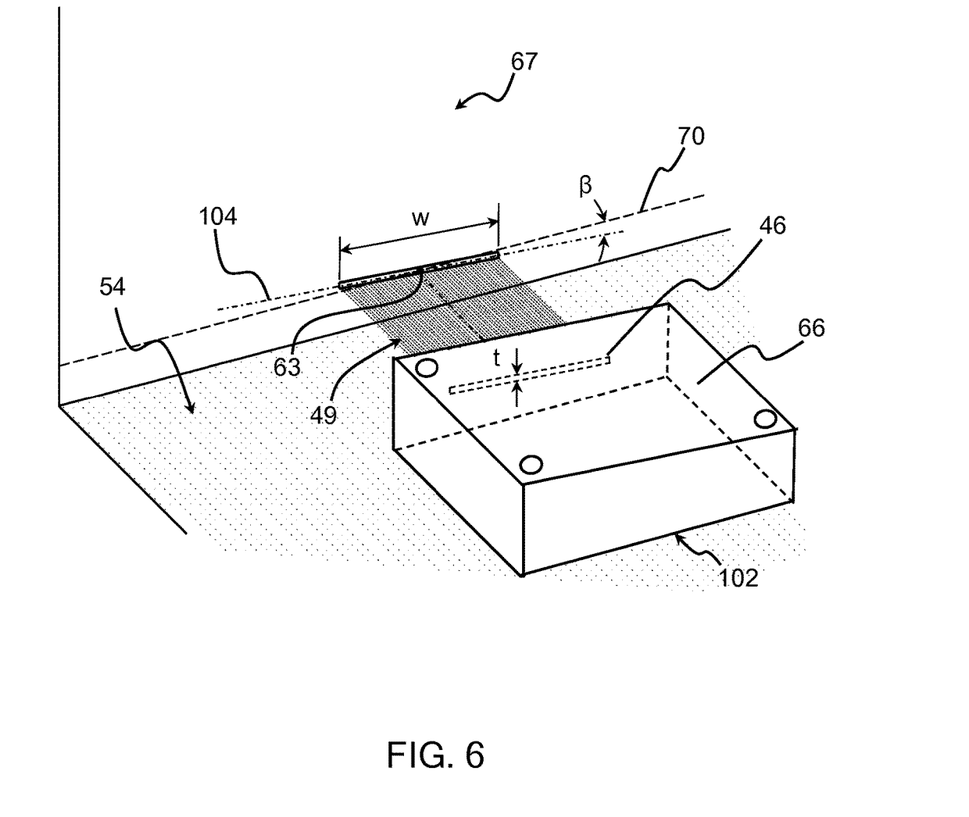
FIG. 6 is a detailed pictorial view of the sheet of light intersecting with a representative workpiece in accordance with the present invention.

Referring now to FIG. 6, a detailed diagrammatic drawing illustrating the light source 46 projected onto a sample planar surface 67 is shown. In this detailed view, the sheet of light 49 is shown projected against the sample planar surface 67 to demonstrate the orientation and properties of the sheet of light 49. The sheet of light 49 is projected along the beam plane 104 and the beam pitch angle β is shown relative to a reference line 70 passing through the sheet of light 49 defining the beam axis 63 being parallel with the mounting plate 56 and inspection plane 54. Though the view illustrated in FIG. 6 does not demonstrate the inspection system in operational context, the view is provided to promote understanding.

In this view, the light source 46 is shown projecting a sheet of light 49 having a width w and a thickness t. The mounting plate 54 is represented to demonstrate the mounting surface 102 of the housing and demonstrates one implementation that may be applied to orient the sheet of light at the beam pitch angle β in relation to the mounting plate and project each sheet of light along the beam plane 104. As previously discussed, the housing 66 implementations introduced herein and others that may conform to the teachings of this disclosure may be adapted to house light sources 46 or detectors 48, but paired inspection devices (e.g. light source 46a and detector 48a) will be mirrored in design to align the light source 46a and the detector 48a facing each other across the test section 60 with the beam axis 104.

Referring back to FIG. 4, the projection of each of the sheets of light being substantially perpendicular to the workpiece angle α and also being offset angularly about the beam axis 63 at the beam pitch angle β provides for significant improvements in inspecting the workpiece 52 profile. By orienting the light sources 46 to project the sheets of light 49 as demonstrated in this disclosure, the information provided by the occluded sheet of light 49 of each of the workpieces 52 received by each of the detectors 48 is substantially improved. The implementation of the beam pitch angle β is of particular importance because it provides for improved measurement of workpiece 52 features especially in the case of threaded workpieces. By aligning the width of each sheet of light 49 substantially with the pitch of the threads, the occluded sheets of light 49 provide more consistent measurement and more detailed information about each workpiece 52. The various implementations of the disclosed inspection system teach of profile detection systems having improved resolution and superior capability to identify non-conforming threaded workpieces.

The angle α of the inspection plane may be adjusted at any time, but primarily, the inspection plane may be adjusted to align with workpieces having different workpiece angles α (e.g. longer shafts with smaller heads, shorter shafts with larger heads, etc.). An adjustment mechanism 68 is attached to the mounting plate 56 comprising a threaded, manually operated assembly allowing for the inspection plane 54 to be adjusted relative to the track 16 for workpieces having different configurations. Though a threaded, manually operated assembly is demonstrated in this implementation, any assembly capable of allowing for angular adjustment about the y-axis may be applied. Though the implementation described herein refers to the profile detection system 50 being attached to a mounting plate 56, other suitable implementations capable of aligning the light sources 46 with the profile test section 60 similar to those disclosed herein may be applied in accordance with the present invention. The orientation of the sheets of light 46 relative the workpiece 52 at the beam angle disclosed herein provides for improved inspection capability, especially when combined with the alignment of the profile inspection system 50 with the inspection plane 54.

The beam pitch angle β configuration of this implementation may provide for improved measurement of the workpiece 52 due to decreased interference among the plurality of light sources 46 and detectors 48. The alignment of the light source 46 and the detector 48 pairs at the beam pitch angle β ensures that the width w each of the individual sheets of light are not projected along the inspection plane 54 collinearly. By angling the light sources 46 and detectors 48 at the beam pitch angle β, each sheet of light 49 may only intersect the other sheets of light along a small portion of the width w of the individual sheets of light 49 as opposed to being projected collinearly along the inspection plane 54. In this implementation, the beam pitch angle β may provide for reduced cross-talk and interference among the light source 46 and detector 48 pairs. The reduced interference among the light source 46 and detector 48 pairs may further provide for improved image quality due to decreased interference and in some cases may reduce the need for multiplexing of the individual light source 46 and detector 48 pairs providing for increased resolution, measurement speed, and improved accuracy.

Referring back to FIG. 5, a detailed pictorial view of a sheet of light 49 is illustrated intersecting with a representative workpiece 52 for evaluation of workpiece 52 conformance in accordance with the teachings of the disclosed invention. The sheet of light 49 illustrated defines a beam axis extending from the light source 46 and intersecting perpendicular to (or nearly perpendicular to) the longitudinal axis 55 of the workpiece 52 in the direction of the side profile shown. The beam thickness t may be emphasized to show detail. The beam thickness t in this implementation and others may vary significantly. In some cases the thickness t may be increased while the detection device is exposed to and only measures a thinner portion of the thickness. Implementations incorporating thicker sheets of light may be advantageous in simplifying alignment of each profile detection pair. From this view, the beam pitch angle β is clearly visible. The sheet of light 49 illustrated is projected at the beam pitch angle β from the light source 46a disposed in the housing 66 attached to the mounting plate 56 shown in FIG. 4. From this view the beam pitch angle β of the sheet of light 49 is shown significantly in alignment with a plurality of threads 74 of the workpiece 52.

The disclosed inspection system 10 and its various implementations provide for an occluded sheet of light 49 to deliver superior profile information related to a broad range of workpieces. Orientation of the sheet of light 49 about the beam axis 104 at a beam pitch angle β allows for improved detection of non-conforming parts through improved measurement quality.

The beam pitch angle β may range from approximately 1.5 to 6.5 degrees to align with various thread pitches of workpieces. In this implementation the beam pitch angle β is preferably between 3 and 4 degrees in order to significantly align with the most common thread pitch angles of threaded workpieces. In a preferred embodiment the beam pitch angle β may also be approximately 3.5 degrees. Though the beam pitch angle β of some of the disclosed implementations may not align perfectly with all fasteners, improved detection of non-conforming parts may be achieved by any of the implementations disclosed herein. This disclosure provides for an inspection system 10 having improved inspection capability to detect outlying or faulty parts. The added benefits of this improved inspection capability may provide for a system wherein defective workpieces can be identified with improved accuracy allowing for general manufacturing quality to improve by minimizing the use of non-conforming threaded workpieces. While it is known that inclination with respect to beam pitch angle β provides benefits when dealing with threaded workpieces 38, such accommodation cannot be accomplished through adjusting the angle of inspection plane 54 for multiple sets of light sources and detectors. While one of the pairs of light sources and detectors could be oriented to accommodate thread pitch angle β, this is not possible where a multiplicity of pairs of such elements is used. While each of the light sources 46 and photodetectors 48 could be independently adjusted to produce angle β when mounted on mounting plate 56, such independent adjustment is very time-consuming, complex, and would require precise alignment between the elements. This invention provides a desired inclination angle β without special adjustment requirements for each of the optical elements.

Figure 7A:
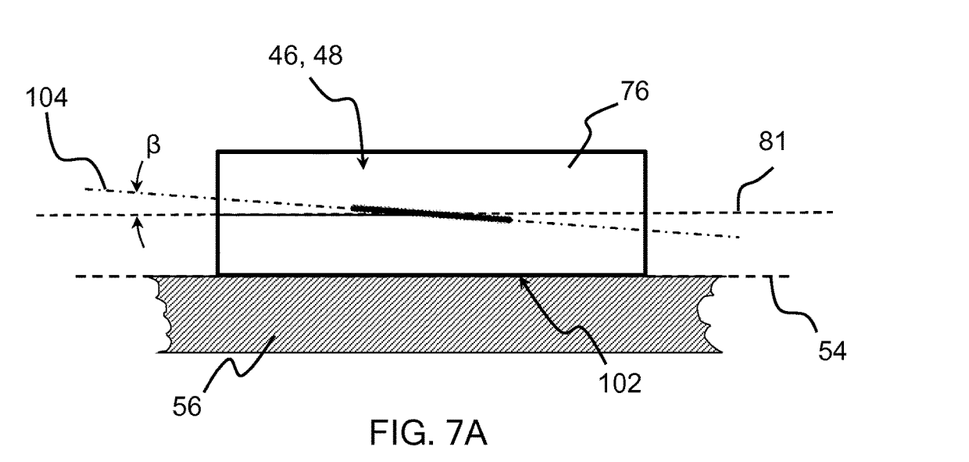
FIGS. 7A, 7B, and 7C are profile drawings of light source housings for the photo detection system of the present invention.
Figure 7B:
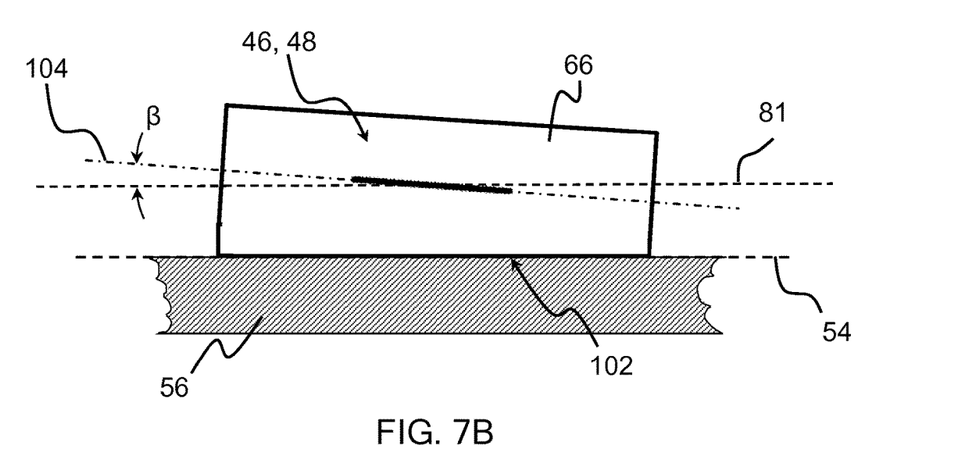
Figure 7C:
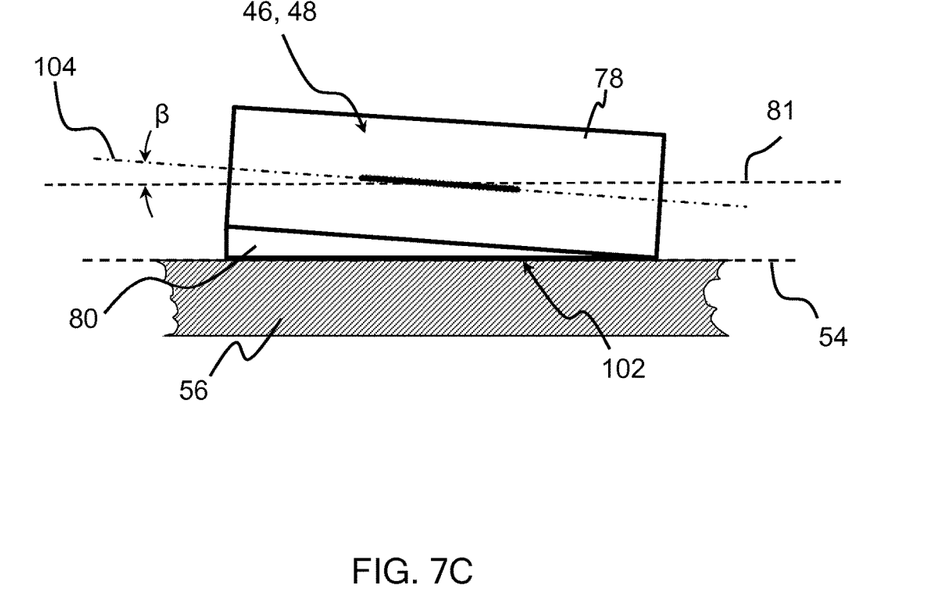

Referring now to FIGS. 7A to 7C, profile drawings of exemplary housings for the light sources 46 and detectors 48 are shown in conformance with the teachings of the disclosed invention. A housing 76 shown in FIG. 7A demonstrates an implementation wherein the light source 46 and detector 48 is angled inside the housing 76 about the beam axis 63. In this implementation the light source 46 and detector 48 is fabricated to provide for a beam pitch angle β between 1.5 and 6 degrees. The beam pitch angle β may also be set to a median beam pitch angle of approximately 3.5 degrees. This orientation is provided by forming housing 66 of both light source 46 and detector 48 with a mounting surface 102 (shown as its bottom surface in FIGS. 7A and 7B) which inclined with respect to the beam plane 104 thereby defining the beam pitch angle β, such that when housing 66 is mounted onto plate 56, beam pitch angle β is provided, without special adjustable mounting provisions. Initial observations have shown that significant improvement in measurement quality can be accomplished by setting the beam pitch angle β to a median angle. In another implementation, FIG. 7B demonstrates the housing 66 creating a beam pitch angle β for the sheet of light about the beam axis equivalent to that of 6A, but the housing 66 is angled relative to the mounting plate 56. Thus beam pitch angle β may be provided and a housing in the form of a rectangular cube (as in FIG. 7A), or one having a mounting surface 102 which is not perpendicular to other surfaces forming the housing. It is noted that only the relative angular orientation between mounting surface 102 and beam plane 104 is significant in defining beam pitch angle β. FIG. 7C demonstrates yet another implementation of a housing 78 incorporating a shim 80 installed between the mounting plate 56 and the mounting surface 102 to angle the sensor housing in relation to the mounting plate 56 at beam pitch angle β. Shim 80 forms mounting surface 102 and a second surface shown as the interface between the shim and the housing which two services are inclined at beam pitch angle β. In FIGS. 7A-7C, a reference line 81 is shown parallel to the mounting plate to provide a reference for the beam pitch angle β. In any of the embodiments the beam pitch angle β is inherently provided by the structure of either housing 78 or shim 80 this providing the beam pitch angle without special adjustment or set up provisions.

Figure 8:
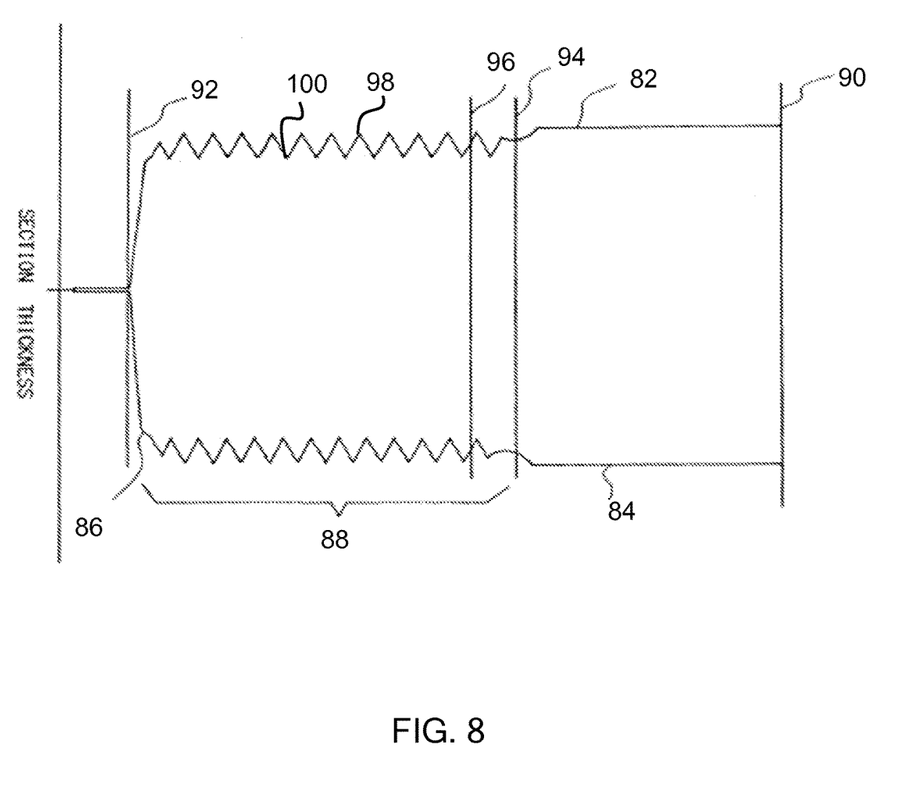
FIG. 8 is a representative output from a photo detector showing a component profile of the present invention.

FIG. 8 shows an example profile of the output of the inspection system 10 generated from an inspection of the workpiece 52. Although curves 82 and 84 together resemble a true profile of the part, it is instead the output of a large number of digitally sampled discrete outputs from a first pair of detectors. In other words, curves 82 and 84 are both plots of substantially one half of the section thickness of workpiece 52 along its detected length. Furthermore, each adjacent plotted analog output is separated by the sampling time required to collect information from the other detectors 48. The profile of curves 82 and 84, however, clearly designate the end 86 of the workpiece 52 as well as threaded portion 88. Although the velocity of the workpiece 52 moving through test section 60 is variable, if its length is known in advance or can be calculated as previously described herein.

Since the profile detection system 50 generates profiles of each workpiece 52, a plurality of groups of curves similar to 82 and 84 are generated simultaneously.

By having multiple sets of curves, form errors of threads in various locations circumferentially about a bolt or fastener may be monitored and detected. Furthermore, through examining differences in the outputs, variations in geometry in radial position on the workpiece can be evaluated. In addition, rotationally symmetric features can be evaluated since it can be assumed that one of the pair of radial detectors 46a, 48a; 46b, 48b; 46c, 48c; or 46d, 48d were to detect the feature. The orientation of the sheets of light relative the workpiece at the beam pitch angle β disclosed herein provides for improved inspection curves. When the sheets of light projected at the beam pitch angle β are combined with the alignment of the profile inspection array 50 with the inspection plane 54, this disclosure provides for improved accuracy in monitoring and detecting workpieces for conformance.

Other important characteristics of the workpiece 52 are also identifiable by the inspection system 10. A proximal end 90 and a distal end 92 may clearly be identified as well as an intermediate portion disposed between a shoulder section and the threaded portion 94 and 96 respectively. The inspection system disclosed herein is capable of measuring and identifying various dimensional characteristics, and primarily provides for improved measurement of threaded workpieces 52. By aligning each sheet of light 49 significantly with the thread pitch defining the beam pitch angle β of each workpiece 52, a crest 98 and root 100 of a thread may be measured across the length of the thread intersected by each of the plurality of light sources 46. The novel arrangement of the profile detection system 50 disclosed herein provides for significant improvements in identifying non-conforming threaded features of workpieces.

As a person skilled in the art will readily appreciate, the above description is meant as an illustration of the principles of this invention. This description is not intended to limit the scope or application of this invention in that the invention is susceptible to modification, variation and change, without departing from spirit of this invention, as defined in the following claims.

What is claimed is:

1. An inspection system for evaluating a workpiece for conformance to configuration criteria, comprising:
   a track configured to translate the workpiece through a test section, the workpiece defining a longitudinal axis;
   an inspection plane formed by a mounting plate being configured to align perpendicular to the longitudinal axis of the workpiece;
   at least two pairs of profile detection devices, each of the at least two pairs comprising a light source as a first profile detection device and a detector as a second profile detection device, the light source being configured to emit a sheet of light along a line defining a beam axis extending parallel to the inspection plane intersecting the longitudinal axis of the workpiece, and the sheet of light having a width extending outward from the beam axis being angled about the beam axis at a beam pitch angle;
   a test section configured to allow the sheet of light emitted by the light source of each pair to be received by the detector paired with the light source, wherein each workpiece translating through the test section occludes the sheet of light and the occluded sheet of light is detected by the detector, and wherein the beam pitch angle is provided for each pair individually by a configuration of a housing of the light source or by a configuration of a housing of the detector, the housing providing the beam pitch angle having a mounting surface for mounting the housing to the mounting plate.

2. The inspection system of claim 1, wherein the beam pitch angle is between 1.5 and 6 degrees.

3. The inspection system of claim 1, wherein the beam pitch angle is between 3 and 4 degrees.

4. The inspection system of claim 1, wherein the beam pitch angle is dimensioned to align the width of the beam with a pitch of a thread disposed in the workpiece.

5. The inspection system of claim 1, wherein each of the detectors of the at least two pairs comprises a photodetector array arranged to align substantially with the sheet of light.

6. The inspection system of claim 1, wherein the profile detection devices of the at least two pairs attached to the mounting plate are evenly spaced about the test section.

7. An inspection system for evaluating a threaded workpiece with a threaded shaft and an enlarged head for conformance to configuration criteria, comprising:
a track configured to translate the workpiece through a test section, the workpiece defining a longitudinal axis;
an inspection plane formed by a mounting plate being configured to align perpendicular to the longitudinal axis of the workpiece;
at least two pairs of profile detection devices, each of the at least two pairs comprising a light source and a detector, the light source being configured to emit a sheet of light along a line defining a beam axis extending parallel to the inspection plane intersecting the longitudinal axis of the workpiece, and the sheet of light having a width extending outward from the axis being angled about the axis at a beam pitch angle;
a test section configured to allow the sheet of light emitted by the light source of each pair to be received by the detector paired with the light source, wherein each workpiece translating through the test section occludes the sheet of light and the occluded sheet of light is measured by the detector, and
wherein the beam pitch angle is provided for each pair individually by a shim for mounting a housing of the light source or of the detector to the mounting plate, the shim having a mounting surface for mounting the shim to the mounting plate and the shim having a second surface adapted to support the housing.

8. The inspection system of claim 7, wherein the beam pitch angle is between 1.5 and 6 degrees.

9. The inspection system of claim 7, wherein the beam pitch angle is between 3 and 4 degrees.

10. The inspection system of claim 7, wherein the beam pitch angle is dimensioned to align the width of the beam with a pitch of a thread disposed in the workpiece.

11. The inspection system of claim 7, wherein each of the detectors of the at least two pairs comprises a photodetector array arranged to align with the sheet of light.

12. An inspection system for evaluating a workpiece in accordance with claim 7, wherein the profile detection devices of the at least two pairs attached to the mounting plate are evenly spaced about the test section.

* * * * *